Figure 1:
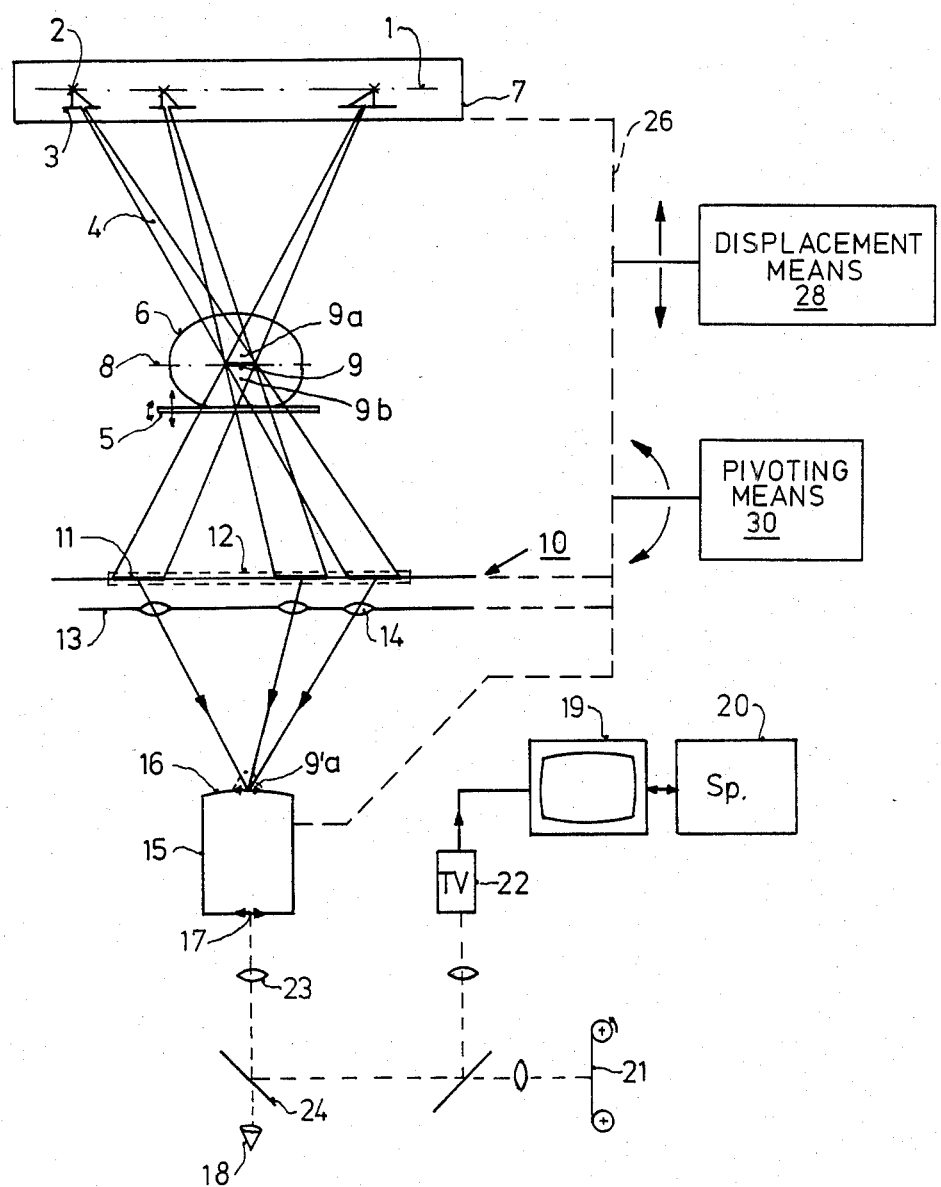

United States Patent [19]
Weiss et al.

[11] Patent Number: 4,513,433
[45] Date of Patent: Apr. 23, 1985

[54] FLUOROSCOPY APPARATUS FOR FORMING LAYER IMAGES OF A THREE-DIMENSIONAL OBJECT

[75] Inventors: Hermann Weiss, Hamburg; Rolf Linde, Haseldorf; Ulf Tiemens, Iserlohn; Erhard Klotz, Halstenbek, all of Fed. Rep. of Germany

[73] Assignee: U.S. Philips Corporation, New York, N.Y.

[21] Appl. No.: 592,319

[22] Filed: Mar. 22, 1984

Related U.S. Application Data
[63] Continuation of Ser. No. 301,853, Sep. 14, 1981, abandoned.

[30] Foreign Application Priority Data
Oct. 4, 1980 [DE] Fed. Rep. of Germany ....... 3037621

[51] Int. Cl.³ .............................................. G03B 41/16
[52] U.S. Cl. .......................................... 378/2; 378/23
[58] Field of Search ...................................... 378/2, 23

[56] References Cited
U.S. PATENT DOCUMENTS
4,132,896  1/1979  Klotz ...................................... 378/2

FOREIGN PATENT DOCUMENTS
2746035  4/1979  Fed. Rep. of Germany .......... 378/2
1572421  7/1980  United Kingdom ..................... 378/2

Primary Examiner—Craig E. Church
Attorney, Agent, or Firm—Jack E. Haken

[57] ABSTRACT

Apparatus for the layer-wise imaging of an object by means of a large number of radiation sources which are situated in a radiation source plane and whose radiation beams intersect one another so that the approximately equally large radiation beam cross-sections which are situated in one irradiation plane almost completely cover one another. A record carrier is arranged on the other side of the object in order to record perspective images produced by the radiation beams. A imaging matrix which comprises imaging elements for the superposition of the perspective images on an image display device is disposed behind the record carrier. Displacement means are provided in order to realize a relative movement between the irradiation plane and the object or an object table carrying the object.

7 Claims, 4 Drawing Figures

FLUOROSCOPY APPARATUS FOR FORMING LAYER IMAGES OF A THREE-DIMENSIONAL OBJECT

This is a continuation of application Ser. No. 301,853, filed Sept. 14, 1981 abandoned.

The invention relates to flouroscopy apparatus for imaging layers of an object using the techniques of tomosynthesis.

BACKGROUND OF THE INVENTION

Such an apparatus for, for example, medical diagnosis or the testing of materials is known from German Offenlegungsschrift 27 46 035. This apparatus is suitable for obtaining layer images of a three-dimensional object within an object zone. The object zones is irradiated from different directions of perspectives with a large number of radiation beams which mutually cover one another. Layer images can then be formed in real time; for example, a frosted glass plate can be moved as desired for the imaging of different object layers. The position of the irradiation plane or the position of the common superposition zone of all radiation beams with respect to the object remains unchanged.

The superposition zone (which is irradiated by all of the radiation beams) has a "rhombic" geometry. The superposition zone tapers from the irradiation plane where the largest dimension of the common superposition zone occurs, as the distance from that irradiation plane increases. Accordingly, the volume which is reconstructed from the perspective images by means of the imaging matrix also has a tapered shape. The image quality of the reconstructed layer images decreases as a function of distance from the irradiation plane, because artefacts are produced in the zone which is not irradiated by all radiation beams and the size of this zone increases with distance from the irradiation plane.

It is an object of the invention to provide a fluoroscopy apparatus which enables the formation of layer images an entire large object, which have consistent quality throughout the object.

This object is achieved in accordance with the invention in that an apparatus of the kind set forth further comprises displacement means for performing a relative movement between the irradiation plane and the object. The displacement means are constructed so that, in any position of the irradiation plane with respect to the object, the imaging elements and the image display device are adjusted for optimum imaging of the irradiation plane.

It is thus achieved that layer images of the same high quality can be obtained of layers which are situated at different locations within an object. To this end, the object is irradiated in a continuous or pulsed manner while the position of the irradiation plane is changed with respect to the object and each time the object layer which is situated within the irradiation plane is reconstructed. The layer images are then directly formed from the coded images. It must be ensured that the irradiation plane is not situated too near to the object surface, because otherwise the radiation load for the object might become excessively high. The position of the irradiation plane in the object can be indicated, for example, by means of a light mark on the object itself. However, it is alternatively possible to indicate in advance a given object zone within which the irradiation plane can be displaced.

The layer images obtained can be processed, for example, electronically and can be displayed on a monitor for the purpose of diagnosis and then electronically stored. After the irradiation, individual layer images can then be fetched for a detailed study. To this end, the image display device is coupled to devices for the display and storage of layer images.

The described fluoroscopy tomosynthesis method is inter alia attractive for use in accident diagnostics, because the physician can very quickly make a diagnosis without time-consuming development of film. The radiation sources are preferably separately activatable, (electrically or mechanically) so that different survey images of the object can also be formed.

Evidently, during fluoroscopy tomosynthesis different layer images can also be formed (in the manner described in German Pat. No. 27 46 035) in each position of the irradiation plane with respect to the object. To this end, for example, the record carrier has a long afterglow time or an image storage effect for the recording of the perspective images, so that it is not continuously necessary to irradiate the object during the formation of the layer images. This operation can be repeated for different positions of the irradiation plane in the object.

In a preferred embodiment in accordance with the invention, the object table is displaceable with respect to the radiation source plane or the radiation sources situated in the radiation source plane are intermittently or continuously displaceable, together with the record carrier, with respect to the object.

As a result, the irradiation plane can be simply displaced as desired with respect to the object, without the position of the irradiation plane with respect to the radiation plane or with respect to the record carrier being changed. This is attractive because coded images at the same scale are obtained wherefrom layer images can be reconstructed at the same scale. To this end, use can be made of an imaging matrix which is arranged at a fixed distance from the record carrier and a layer image display device (for example, a frosted glass plate) which is arranged in a fixed position with respect thereto.

Figure 2:
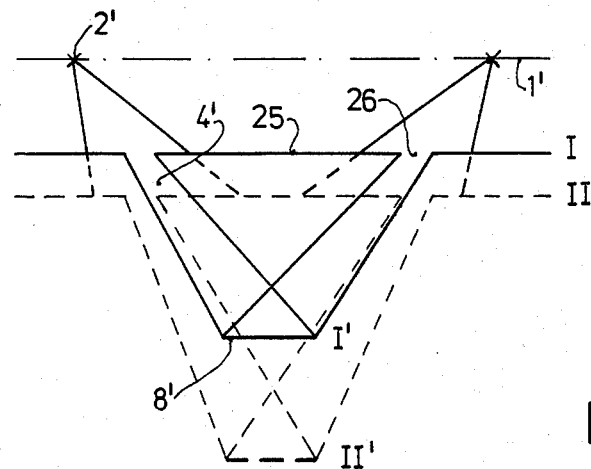
Figure 3:
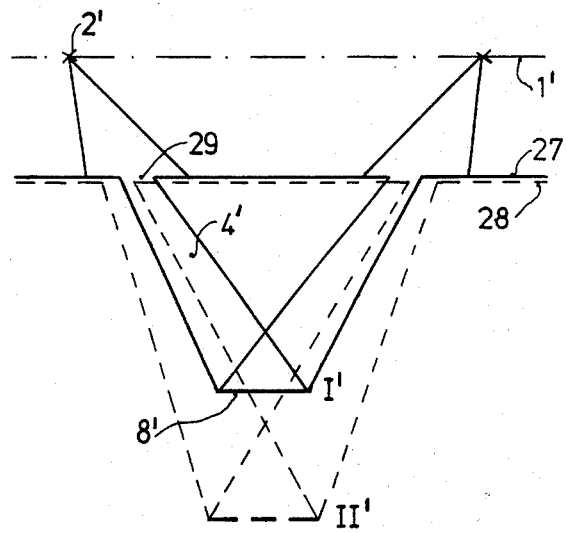
Figure 4:
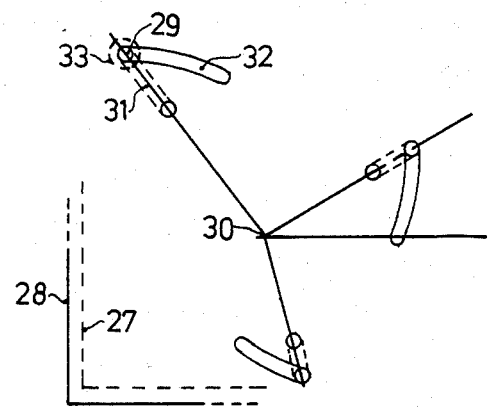

The drawing shows embodiments in accordance with the invention. Therein:

FIG. 1 shows a fluroroscopy apparatus for making real-time layer images of a three-dimensional object, FIG. 2 shows a diaphragm plate whose height can be adjusted for the displacement of the irradiation plane with respect to the object, FIG. 3 shows a further diaphragm device for the displacement of the irradiation plane with respect to the object, and FIG. 4 shows a special embodiment of the further diaphragm device.

FIG. 1 shows a fluoroscopy apparatus in accordance with the invention for forming real time layer images of a three-dimensional object. The apparatus comprises several, for example, twenty-five radiation sources 2 which are arranged in a single radiation source plane 1 and whose radiation beams 4 are collimated by diaphragms 3 to irradiate an object 6 from different directions. The object 6 is arranged on an object table 5. The radiation sources 2 may be, for example, X-ray sources which are arranged in a common tank 7, and the object 6 may be a human body. The radiation beams 4 irradiate the object 6 so that the cross-sections of the radiation beams 4 in the irradiation plane 8 which will be present within the object 6 are approximately equally large and almost completely cover one another. The radiation beams 4 then define a common superposition zone 9 which has its largest dimension in the irradiation plane 8 and which decreases in size as the distance from the irradiation plane increases (zones 9a, b).

The beams 4 pass through the object 6 and are incident on a record carrier 10 where they form a coded image 12 which consists of individual separate or superposed perspective images 11. The record carrier 10 may be, for example, a flat luminescent screen which is arranged parallel to the radiation source plane 1 and which converts X-rays into visible light alternately the record carrier may be an image intensifier tube which produces a visible image of the radiation pattern which is incident on its entrance screen. A scatter radiation grid may be disposed between the object 6 and the record carrier 10 in order to reduce the scatter radiation incident on this unit.

An imaging matrix 13, (for example, a lens matrix whose imaging elements 14 (which may be high-power objectives) are arrange at a reduced scale in the matrix plane in accordance with the flat distribution of the radiation sources 2 is disposed behind the record carrier 10 at a fixed distance therefrom and parallel thereto. The prespective images 11 are superposed using the imaging elements 14 so that the object volume irradiated by the radiation beams 4 is reconstructed. FIG. 1 shows only the object volume 9a as the reconstructed volume 9'a.

Other devices such as, hole diaphragm devices as known, for example, from German Offenlegungsschrift 27 46 035 may altenatively be used as imaging matrices for the layer image reconstruction.

A layer image display device 15, for example, a frosted glass plate or a suitable electronic image pickup device is positioned within the reconstructed object volume to display of layer images. It is arranged at a fixed distance from the record carrier 10 or from the imaging matrix 13 so that the object layer which is situated in the common superposition zone 9 of all radiation beams 4 is reconstructed.

If several layers of the object 16 are to be reconstructed, the irradiation plane 8 or the superposition zone 9 is displaced with respect to the object 6. To this end, the radiation source tank 7, the record carrier 10, the imaging matrix 13 and the layer image display device 15 can be combined to form one structural unit and occupy a fixed position with respect to one another (indicated schematically by dashed lines 26). The displacement between the irradiation plane 8 and the object 6 is then realized by displacement of the complete structural unit with respect to the stationary object 6. On the other hand, the object 6 may also be displaced with respect to the stationary structural unit so that, for example, the distance between the object table 5 and the radiation source plane 1 is changed or the object table 5 is tilted or pivoted. The structural unit can also be additionally tilted or pivoted with respect to the stationary object 6. The displacement, tilting or pivoting can be realized by means of suitable mechanical or electromechanical displacement means 28, 30 during the observation of the instantaneously obtained layer images.

During the displacement of the irradiation plane 8 and the object 6 with respect to each other, all radiation sources can be continuously operated, i.e. they may be constantly switched on. The object 6 is then continuously irradiated and the layer images 17 displayed by means of the layer image display device 15 can be directly observed (18), or displayed on a monitor 19 or electronically stored in a memory 20 (for example, video tape or video disc) or be recorded directly on a film 21. The electronic images can also be transferred to a film by means of a hard copy apparatus. For further processing, the layer images 17 presented on the exit by the layer image display device 15 can be recorded by means of an electronic camera 22. The beam paths between the individual image processing elements 15, 18, 21 and 22 have been shown only diagrammatically for the sake of clarity and may comprise the customary imaging means (lenses 23) and beam splitters or beam deflectors 24.

The radiation sources 2 may altenatively be operated in a pulsed manner, i.e. they may be consecutively switched on at small intervals. This is advantageous if a very large number of layer images must be formed for an object. The object displaced during each of the irradiation intervals; and radiation load for the object is then reduced with respect to the continuous irradiation mode. The relative movement between the irradiation plane 8 and the object 6 can be realized automatically and at a constant speed, for example, in order to obtain a series of parallel layer images.

All layer images formed by means of the apparatus in accordance with the invention shown in FIG. 1 have the same scale and the same image quality with respect to each other, because the radiation geometry is not changed during the relative movement between the irradiation plane 8 and the object 6. When use is made of lenses as the imaging elements 14, the layer images are always reconstructed with maximum focus in the depth of focus range of the lenses or in the imaging plane. In the apparatus which is known from German Offenlegungsschrift 27 46 035, this is applicable only to layer images up to a comparatively small distance from the irradiation plane. Therein, reconstruction images of object layers which are situated further from the irradiation plane are not sharp.

The entrance plane of the layer image display device 15 can be arranged to be pivotable so that so-called oblique layers which are situated at an angle with respect to the irradiation plane 8 can be reconstructed; however, these oblique layers must still be present within the depth of focus range of the lenses 14.

FIG. 2 shows a further multiple radiation source which, for the sake of clarity, is shown to comprise only two X-ray sources 2' which are situated in one radiation source plane 1'. Parallel to the radiation source plane 1' there is arranged a diaphragm plate 25 of the kind known from German Auslegeschrift 27 28 999 in order to form or collimate radiation beams 4' which irradiate the object (not shown), the cross-sections of said beams being equally large and fully cover each other in a common irradiaton plane 8'. The diaphragm apertures 26 are distributed in the diaphragm plate 25 in accordance with the flat radiation source distribution (at a reduced scale).

The diaphragm plate 25 is arranged to be displaceable perpendicularly to the radiation source plane 1' for the displacement of the irradiaton plane 8' with respect to the object. When it is moved, for example, from the position I to the position II (i.e. further away from the radiation source plane 1') the irradiation plane 8' is simultaneously displaced from the position I' to the position II' which are both situated within the stationary object (not shown). Because the irradiation plane 8' is then displaced not only with respect to the object but also with respect to the radiation source plane 1' or the record carrier 10 (FIG. 1), the position of the perspective images 11 in the entrance plane of the record carrier 10 is also changed. In order to enable reconstruction of that object layer which is each time situated in the irradiation plane 8', therefore, either the distances of the imaging matrix 13 and of the layer image display device 15 from the record carrier 10 must be changed accordingly or, with a fixed distance between the imaging matrix 13 and the record carrier 10, each time the distances between the imaging elements 14 themselves in the matrix plane must be changeable true to scale (for example, as described in German Patent Application P 29 46 442.4) and additionally the distance between the record carrier and the layer image display device must be changeable.

The same is applicable to the diaphragm device which is shown in the FIGS. 3 and 4 and which consists of two diaphragm plates 27, 28 which are arranged to be parallel with respect to each other and with respect to the radiation source plane 1'. This diaphragm device enables a true-to-scale variation of the distribution of the diaphragm aperture 29 in the plane of the diaphragm device. The distribution again corresponds to the flat distribution of the radiation sources 2'.

To this end, for example, the diaphragm plate 27, is situated underneath the diaphragm plate 28 in FIG. 4 (denoted by broken lines) and comprises slit-like apertures 31 which extend radially with respect to the centre 30 of the diaphragm plate 27, while the diaphragm plate 28 comprises slit-shaped apertures 32 which are arranged in helical manner and which intersect the radially extending slits 31. At the area of intersecton of the two apertures 31 and 32, a cam engages in order to obtain a desired diaphragm aperture 29 which also comprises a sleeve 33 for covering further resultant apertures of the slits 31, 32. By rotation of the two diaphragm plates 27, 28 about an axis which extends perpendicularly to the plate surface and through the centre 30, said centre corresponding to the centre of the radiation source distribution, the distribution of the diaphragm apertures 29 can be changed true to scale. FIG. 4 shows a total of three diaphragm apertures 29 for the sake of clarity.

What is claimed is:

1. Apparatus for layer-wise imaging of an object (6) comprising:

a plurality of radiation source means (2), which are disposed adjacent the object in a single radiation source plane (1), each of which projects a beam (4) of penetrating radiation through the object in a geometry wherein all of the radiation beams have approximately the same cross section area in an irradiation plane (8) which intersects the object and all of the beams cover substantially the same region of the irradiation plane;

record carrier means (10), disposed on the opposite side of the object from the radiation source plane to receive the radiation beams which have passed through the object and to record therefrom perspective images of the object which are formed by the radiation beams;

image display means (15) including an image receiving surface (16);

imaging matrix means (13), comprising a plurality of imaging elements (14) which are disposed in a geometry which corresponds to the distribution of the radiation source means in the radiaton source plane, whih produce an image of a layer within the object by superpositioning the perspective images on the image receiving surface; and means (28) for producing a relative displacement between the position of the irradiation plane and the object in a direction perpendicular to the irradiation plane.

2. The apparatus of claim 1 wherein the radiation source means, the record carrier, and the imaging matrix means form a single structural unit and occupy fixed positions with respect to one another and wherein the means for performing a relative displacement displace the structural unit with respect to the object.

3. The apparatus of claim 1 further comprising a planar diaphragm disposed parallel to the radiation source plane between the radiaton source plane and the object, said diaphragm defining a plurality of apertures which are distributed therein and function to form the radiation beams; and means for displacing the position of the apertures in the plane of the diaphragm to change the distances between the various apertures while maintaining the angular relationship therebetween to affect a true-to-scale variation in the size of the distribution of apertures.

4. The apparatus of claim 1 further comprising means for rotating the radiation source means and the record carrier with respect to the object.

5. The apparatus as claimed in any one of claims 1 through 3 wherein the record carrier comprises a material having an afterglow time which is sufficiently long to effect storage of the perspective images after an irradiation.

6. The apparatus as claimed in any one of claims 1 through 3 wherein the image display means is an image intensifier.

7. The apparatus of claim 1 wherein the imaging elements comprise objective lenses.

* * * * *